United States Patent
Wei et al.

(10) Patent No.: US 8,038,579 B2
(45) Date of Patent: Oct. 18, 2011

(54) SYSTEM FOR TRAINING AND EVALUATING BILATERAL SYMMETRIC FORCE OUTPUT OF UPPER LIMBS

(75) Inventors: Shun-Hwa Wei, Taipei (TW); Wen-Hsu Sung, Taipei (TW); Wen-Wei Tsai, Taipei (TW); Hsiu-Wen Tseng, Taipei (TW)

(73) Assignee: National Yang Ming University, Taipei (TW)

( * ) Notice: Subject to any disclaimer, the term of this patent is extended or adjusted under 35 U.S.C. 154(b) by 0 days.

(21) Appl. No.: 12/633,624

(22) Filed: Dec. 8, 2009

(65) Prior Publication Data

US 2011/0136626 A1    Jun. 9, 2011

(30) Foreign Application Priority Data

Dec. 4, 2009 (TW) .................... 98141580 A

(51) Int. Cl.
*A63B 71/00* (2006.01)
*A61H 1/00* (2006.01)
*A61H 1/02* (2006.01)
*A61H 5/00* (2006.01)

(52) U.S. Cl. ............................. 482/9; 601/33

(58) Field of Classification Search .................. 482/1–9; 601/23, 33–35; 434/247; *A63B 71/00; A61H 1/00, A61H 1/02, 5/00*
See application file for complete search history.

(56) References Cited

U.S. PATENT DOCUMENTS

| 5,254,066 | A | * | 10/1993 | Brown et al. | 482/137 |
| 5,421,798 | A | * | 6/1995 | Bond et al. | 601/23 |
| 5,484,355 | A | * | 1/1996 | King et al. | 482/4 |
| 5,957,812 | A | * | 9/1999 | Harrigan | 482/8 |
| 7,121,981 | B2 | * | 10/2006 | Whitall et al. | 482/8 |
| 7,666,118 | B1 | * | 2/2010 | Anthony | 482/8 |
| 2003/0028130 | A1 | * | 2/2003 | Wunderly et al. | 601/5 |
| 2008/0161733 | A1 | * | 7/2008 | Einav et al. | 601/34 |

OTHER PUBLICATIONS

The Merriam-Webster Dictionary, http://www.merriam-webster.com/dictionary/index.*

* cited by examiner

*Primary Examiner* — Stephen Crow
*Assistant Examiner* — Oren Ginsberg
(74) *Attorney, Agent, or Firm* — Hogan Lovells US LLP

(57) ABSTRACT

A system for training and evaluating bilateral symmetric force output of upper limbs has a force application unit of bilateral upper limbs, a movable link unit, a signal conversion unit, a computing unit and a driving unit. The force application unit of bilateral upper limbs has at least two force sensors. When stroke patients perform training, the system can instantaneously measure values of forces exerted by users and sensed by the sensors, and determine if the movable link unit is driven according to a pre-configured training pattern, so that both hands of patients are allowed to perform training movements pushing forward and pulling backward to promote training mechanism of dual-brain hemisphere organization and improve moving capability of upper limb of affected side.

13 Claims, 3 Drawing Sheets

SYSTEM FOR TRAINING AND EVALUATING BILATERAL SYMMETRIC FORCE OUTPUT OF UPPER LIMBS

FIELD OF THE INVENTION

The present invention is related to the field of rehabilitation medicine and medical engineering, and more particularly to a system adopted to stroke patients for training and evaluating bilateral symmetric force output.

BACKGROUND OF THE INVENTION

Cerebrovascular disease is commonly known as stroke indicating acute or chronic brain nerve cell necrosis as a result of cerebrovascular occlusion or cerebrovascular rupture. Usually, stroke results in partial or total brain disorder. In severe case, it may lead to sudden death. Healthy brain cells unaffected by stroke may stand a chance of neural plasticity. After stimulation treatment, cortex reorganization might happen to speed up recovery of affected function. Clinically, targeting at recovery training of mobility of stroke patient, therapists combine various therapy theories and techniques to instruct and assist stroke patient to re-learn, adjust with appropriate movement pattern and prohibit inadequate posture. Therefore, the effectiveness of motor re-learning can be achieved. Alternatively, given other sensory participation, effective replacing skill and auxiliary equipment, life skills of stroke patients can be rebuilt to live independent life again.

Later on, scholars combine fundamental theories to further develop diversified treatment techniques, among which compensatory strategies, constraint induce movement therapy (CIMT) and bimanual therapy are three treatment patterns that are widely accepted.

The compensatory strategies reply on the replacement of unaffected side or adjustment of environmental equipment, and increase life independence of stroke patients in the beginning stage. However, excessive dependence prevents affected side from being stimulated and learning subsequently, thereby lowering the degree of recovery of affected side.

The CIMT has been proved to help generate self-movement of patients induced at acute stage of stroke. However, lacking of the reference standard of movement of unaffected side and training of mutual coordination of both sides, the simulation effectiveness of functional movement of daily life associated with patients having higher functional capability at chronic stage is still questioned in doubt. The bimanual therapy is extensively applied to a bimanual movement pattern commonly available in life as training movement thereof, facilitating extension of functional movement of daily life. Also accompanying with training mechanism of dual-brain hemisphere organization, the bimanual therapy is deeply admired by scholars supporting movement learning. However, the actual training and evaluation thereof need be further developed and refined.

Mudie and Matyas gave regular auditory stimulus to stroke patients in 1996, and additionally mounted a movable handle to a self-developed platform for patients to use both hands to perform bilateral equal momentum training featured by using both hands to push and pull with identical movement. As such training pertains to the design of general mechanism, applied force and distance of operation fail to be precisely quantized.

Cauraugh and Kim treated the limbs of affected side of patients with neuromuscular stimulation in 2002, and let the patients to perform bilateral movement training in collaboration with the hand of unaffected side. At last, a block and box test is used to evaluate the effectiveness of the training. Throughout the evaluation process, as observing the number of moving blocks is the only means to evaluate the improved degree of patients and no other instrument involved in measuring force or distance, it is indeed uneasy to ascertain if both hands of patients actually perform bilateral movement or the hand of unaffected side guides the hand of affected side to perform bilateral movement training. Hence, such training may have little significance and fails to accurately quantize effectiveness. Lately, a newly developed movement training mechanism for bilateral upper limbs combined with visual feedback is available, so that both hands of patients hold handles at two ends of a support bar to perform the movement training along left, right, forward and backward directions. Despite being amusing for combining with visual feedback, it is still uncertain if patients use both hands to perform bilateral movement or the hand of unaffected side guides the hand of affected side to perform bilateral movement training. As a result, the training effect is lessened, and the effectiveness of the rehabilitation training fails to be objectively quantized.

Rose brought up another approach in 2005. He put a LED button on a table and requested testees to sit in front of the table. When a light is on, testees are requested to press the LED button with both hands at the same time so as to turn off the light with the fastest speed. The response time of movement and the movement performing time can thus be observed. As such means is uncertain if both hands simultaneously press the button to turn off the light, the starting time of movement recorded for the response time is counted when the movement of the testees is viewed to start by the naked eyes of the testers. Consequently, the way of counting time fails to precisely record the actual performing time duration of testees.

From the above approaches, it is understood that trainings performed clinically at present fail to precisely quantize the training process and the results thereof, and thus fail to ascertain if hands of both sides of patients actually perform bilateral movement or the hand of unaffected side guides the hand of affected side to perform bilateral movement training. Therefore, the hand of affected side fails to be treated with effective training.

SUMMARY OF THE INVENTION

To improve the foregoing disadvantages, the present invention discloses a system for training and evaluating bilateral symmetric force output of upper limbs. The system at least has a force application unit of bilateral upper limbs, a force application unit of bilateral upper limbs, a movable link unit, a signal conversion unit, a computing unit and a driving unit.

The force application unit of bilateral upper limbs has at least two force sensors. When stroke patients perform training, the system can instantaneously measure values of forces exerted by the patients to the sensors to configure a training pattern beforehand, and determine if the movable link unit is driven, so that both hands of patients are allowed to perform training movements pushing forward and pulling backward to promote training mechanism of dual-brain hemisphere organization and improve moving capability of upper limb of affected side.

The present invention is advantageous in providing adaptive adjustment having rehabilitation training protocol for training to tailor training pattern, time duration and intensity according to individual condition of stroke patients. While stroke patients perform rehabilitation training, the system of the present invention adopts visual and auditory means to provide bilateral symmetric force output information of upper limbs so that patients can always adjust the force outputs of unaffected side and affected side. As for evaluation, an instantaneous, quantized evaluation interface addressed to provide the symmetry index of bilateral force output of upper limbs serves to assess the degree of recovery of stroke patients upon performing different movements of upper limbs. After performing the training, patients can be immediately aware of the evaluation result of movements of their upper limbs so as to achieve an objective and quantized evaluation.

The foregoing and other features and advantages of the present invention will be more clearly understood through the following descriptions with reference to the drawing, wherein:

DETAILED DESCRIPTION OF THE PREFERRED EMBODIMENT

Figure 1:
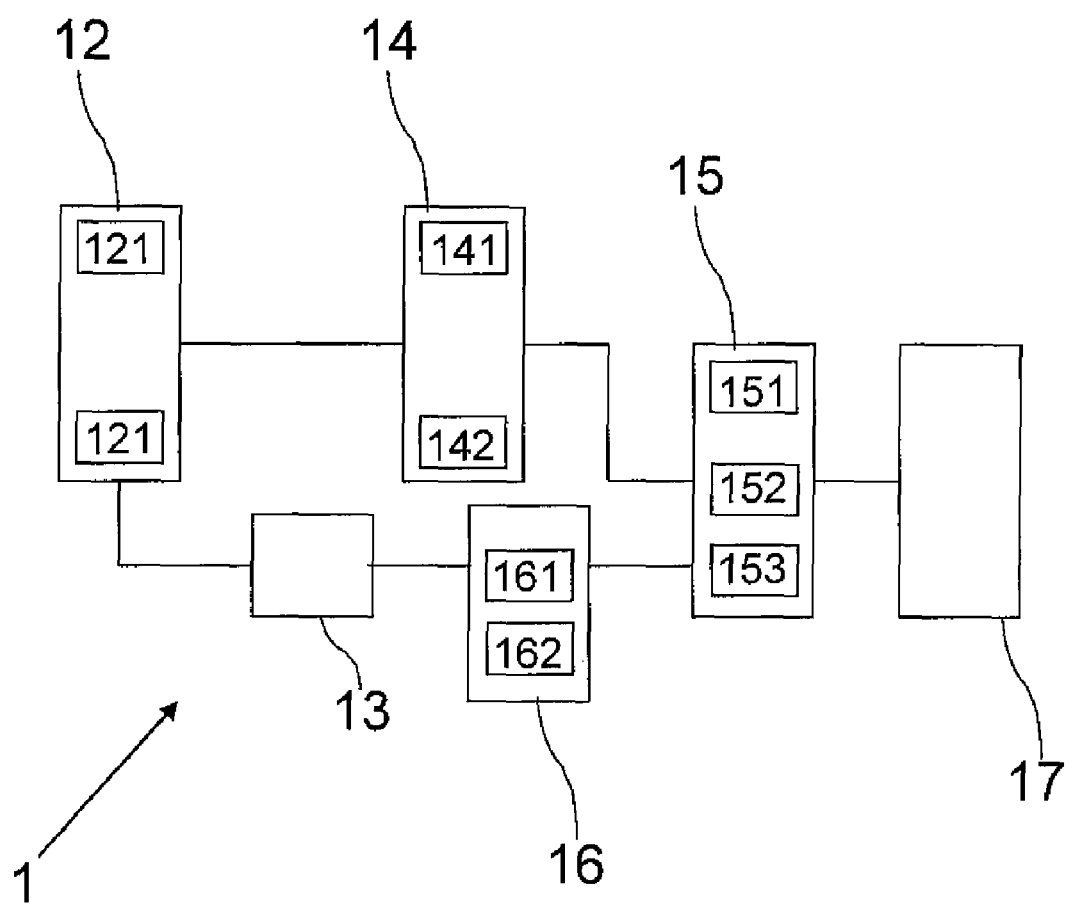
FIG. 1 is a block diagram of a preferred embodiment of a system for training and evaluating bilateral symmetric force output of upper limbs in accordance with the present invention.
Figure 2:
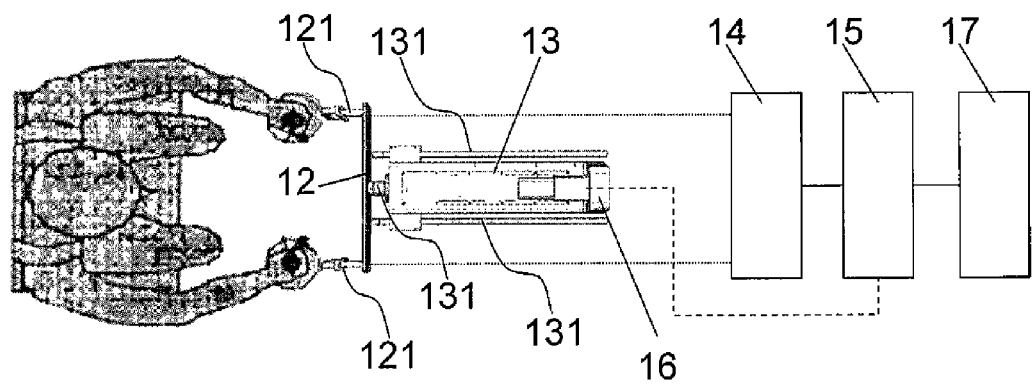
FIG. 2 is a schematic view illustrating that a user operates the system in FIG. 1.

With reference to FIGS. 1 and 2, a system for training and evaluating bilateral symmetric force output of upper limbs (1) of an embodiment in accordance with the present invention has a force application unit of bilateral upper limbs (12), a movable link unit (13), a signal conversion unit (14), a computing unit (15) and a driving unit (16).

In the embodiment, the force application unit of bilateral upper limbs (12) has at least two force sensors (121). The force sensors (121) are adopted to measure a value of a force exerted by a user. To facilitate the forces acted on the force sensor when users push or pull, the force sensor may be further connected with a member, including but not limited to a handle, a rocker and the like.

The movable link unit (13) has a plurality of movable links (131). One end of the movable link unit (13) is coupled to the force application unit of bilateral upper limbs (12), and the other end thereof is coupled to the driving unit (16).

The signal conversion unit (14) is adopted to convert values of forces exerted by users into a series of electrical signals. The signal conversion unit (14) further has a signal amplifier (141) or a signal filter (142) to amplify or filter the electrical signals measured by the force measuring device (121).

The computing unit (15) is adopted to compute the electrical signals generated by the signal conversion unit (14) to generate a determination result. Preferably, the computing unit (15) is but not limited to a computer embedded with training and evaluation software for instantaneously generating a determination result. The computing unit (15) further has a spindle control card (151) and a signal fetching card (152). The signal fetching card (152) is coupled to the signal conversion unit (14) to fetch the amplified and filtered electrical signals and forward them to the computing unit (15) in generation of a determination result. The spindle control card (151) is coupled to the driving unit (16). Based on the determination result, a motor module (161) and a power supply module (162) inside the driving unit (16) are controlled by the spindle control card (151). Hence, the movable link unit (13) is driven to enable users' pushing and pulling movement, or the movable link unit (13) is locked to disenable users' pushing and pulling movement. The computing unit (15) further has a database module (153) to store the operation history, including but not limited to a value of a force exerted by a user, default parameters, personal information and the like.

The system of the present invention (1) further has an output unit (17) outputting the determination result or a command instructing users to perform predetermined movement, and providing bilateral symmetric force output of upper limbs for patients to adjust force outputs of unaffected side and affected side at any time. The output patterns include but not limited to image, voice, graph and the like.

Figure 3:
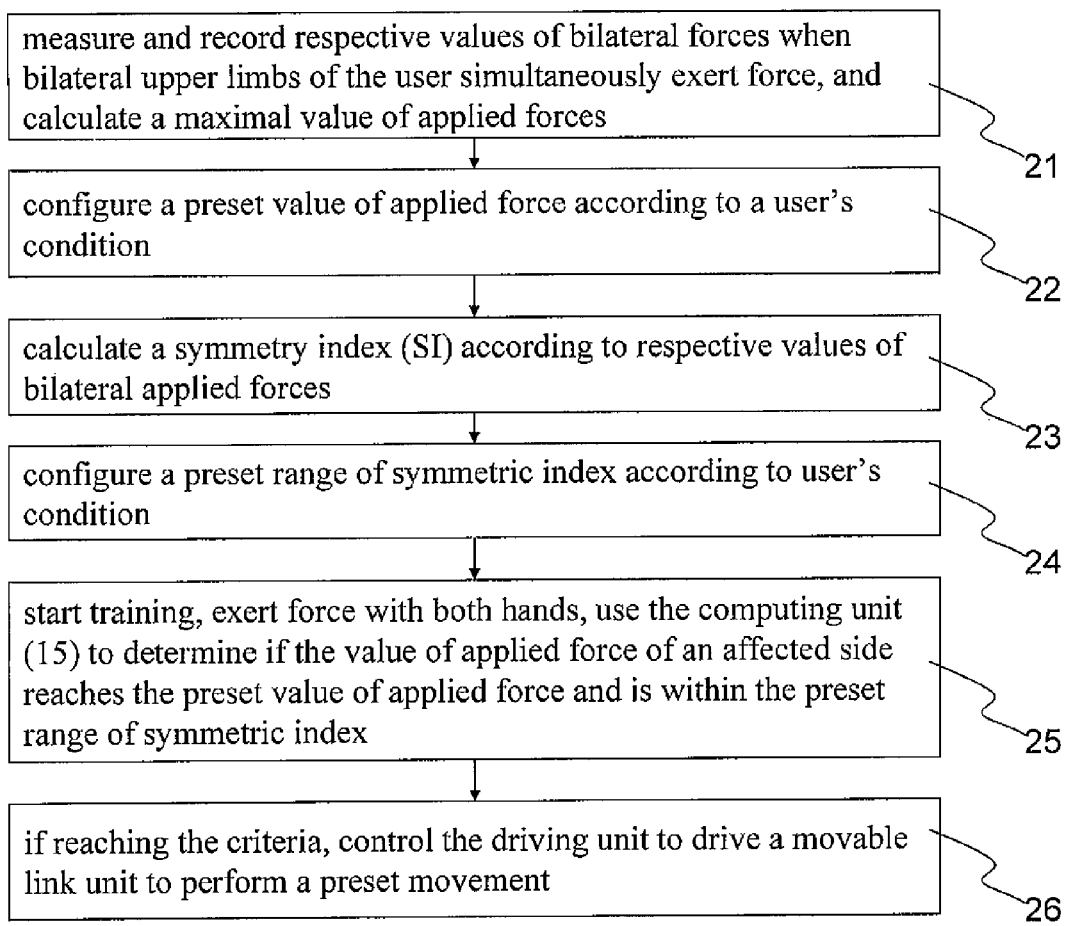
FIG. 3 is a flow diagram of a method for training and evaluating bilateral symmetric force output of upper limbs in accordance with the present invention.

With reference to FIG. 3, how the computing unit (15) of the present invention generates a determination result can be more comprehensive. A method for training and evaluating bilateral symmetric force output of upper limbs has the following steps:

step (21): perform a preset setting targeting at a user's condition prior to training and evaluation, measure and record respective values of bilateral forces when bilateral upper limbs of the user simultaneously exert force, and calculate a maximal value of applied forces; the maximal value of applied forces equals to the maximal applied force value of the unaffected side multiplied by 75% (From the research in the past, the maximal value of force exerted by both hands is 75% of the maximal value of force exerted on single side); the maximal applied force value of the unaffected side is the maximal pushing or pulling force of the upper limb of the unaffected side;

step (22): configure a preset value of applied force according to a user's condition; define the preset value of applied force as a value of applied force, which is reachable by the hand of an affected side of users; the preset value of applied force equals to the aforementioned maximal value of applied force multiplied by an appropriate percentage; the percentage may be adjusted according to user's condition;

step (23): calculate a symmetry index (SI) according to respective values of bilateral applied forces; the symmetry index is obtained from a symmetry value (SV); detailed definition of both is defined as follow:

the symmetry value (SV) of bilateral symmetric force output of upper limbs is defined as a percentage represented by the portion of the value of force exerted by the hand of an affected side in the value of total force exerted by both hands, and the unit thereof is in %;

$$SV = \frac{F_A}{F_A + F_S} \times 100\,(\%)$$

wherein $F_A$ represents the value of force exerted by the hand of an affected side, and $F_S$ represents the value of force exerted by the hand of an unaffected side;

the closer the symmetric value (SV) of bilateral symmetric force output of upper limbs approaches to 50%, the more equivalent and symmetric the value of applied force of an affected side ($F_A$) and the value of applied force of an unaffected side ($F_S$) are; usually, the symmetric value (SV) of bilateral symmetric force output of upper limbs is less than 50%; the ideal symmetric value of applied forces is 50%;

the symmetric index (SI) of bilateral symmetric force output of upper limbs is defined as the ratio between the symmetry value (SV) of bilateral symmetric force output of upper limbs and the ideal symmetric value of applied forces (50%):

$$SI = \frac{SV}{50} \times 100\,(\%)$$

the more the symmetric index (SI) of bilateral symmetric force output of upper limbs approaches to 100%, the more symmetric the value of applied force of an affected side ($F_A$) and the value of applied force of an unaffected side ($F_S$) are; usually, the symmetry value (SV) of bilateral symmetric force output of upper limbs is less than 50%; therefore, the symmetric index (SI) of bilateral symmetric force output of upper limbs is usually less than 100%;

step (24): configure a preset range of symmetric index according to user's condition; the preset symmetric index is an average value of symmetric indices obtained in a fixed time duration (e.g. 10 seconds); after obtaining the average value, further configure a tolerance of the preset symmetric index according to user's condition, for example ±10% and so on;

step (25): start training, exert force with both hands, use the computing unit (15) to determine if the value of applied force of an affected side reaches the preset value of applied force and is within the preset range of symmetric index; the computing unit (15) records both the value and the preset range in the force exerting process; after reaching the foregoing criteria, the computing unit (15) sends a determination result to a driving unit (16);

step (26): if reaching the criteria, control the driving unit to drive a movable link unit to perform a preset movement; the preset movement defines user's pushing and pulling movement; if failing to reach the criteria, keep the system idle until reaching the preset value of applied force and being within the preset range of symmetric index.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A system for training and evaluating bilateral symmetric force output of upper limbs, comprising:
   a force application unit of bilateral upper limbs, said unit having at least two force sensors adapted for measuring values of forces exerted by a user's upper limbs;
   a movable link unit coupled to the force application unit of bilateral upper limbs and having a plurality of movable links;
   a signal conversion unit coupled to the force sensor adapted for converting the values of the forces exerted by the user into a series of electrical signals;
   a computing unit having a computer embedded with training and evaluation software and a database module for storing a force value of the user; said computing unit having:
   a signal fetching card coupled to the signal conversion unit to fetch the electrical signals of the signal conversion unit and forward them to the computing unit in generation of a determination result, wherein the computing unit respectively records values of forces into the database module which were exerted by a left upper limb and a right upper limb and measured by the force sensors, calculates a maximum value of applied force according to the values of forces exerted by the left upper limb and the right upper limb, and configures a preset value of applied force according to a user's condition, the computing unit computing a means for calculating a symmetric index according to the values of the forces exerted by the left upper limb and the right upper limb; and
   a driving unit driving the movable link unit according to the determination result of the computing unit;
   wherein the computing unit determines if values of the forces exerted by the left upper limb and the right upper limb of the user reach the preset value of applied force and the symmetric index is within a range of the preset symmetric index according to the determination result, and controls the driving unit to drive the movable link unit to perform the predetermined movements.

2. The system as claimed in claim 1, wherein the values of the forces exerted by the user comprises a value of a force exerted by a left upper limb and a value of a force exerted by a right upper limb of the user.

3. The system as claimed in claim 1, wherein the signal conversion unit further comprises a signal amplifier.

4. The system as claimed in claim 1, wherein the signal conversion unit further comprises a signal filter.

5. The system as claimed in claim 1, wherein the driving unit further comprises a motor module.

6. The system as claimed in claim 1, wherein the driving unit further comprises a power supply unit.

7. The system as claimed in claim 1, wherein the computing unit further comprises a spindle control card for controlling the driving unit to drive the movable link unit to perform predetermined movements.

8. The system as claimed in claim 7, wherein the predetermined movements comprise movements pushing forward and pulling backward.

9. The system as claimed in claim 1, wherein configuring the preset value of applied force equals to the maximum of applied force multiplied by a percentage.

10. The system as claimed in claim 1, wherein the computing unit further computes a preset symmetric index being an average value obtained from the symmetric indices of the user within a fixed time duration.

11. The system as claimed in claim 1, wherein the range of the preset symmetric index is adjusted according to the user's condition.

12. The system as claimed in claim 1 further comprising an output unit for outputting an evaluation result or an instruction instructing users to perform predetermined movements.

13. The system as claimed in claim 1, wherein the database module is further adapted to store the user's operation history.

* * * * *